(12) United States Patent
Harding et al.

(10) Patent No.: US 7,172,611 B2
(45) Date of Patent: Feb. 6, 2007

(54) SURGICAL SCALPEL ASSEMBLY

(75) Inventors: Weston F. Harding, Lehi, UT (US); Christopher N. Cindrich, Draper, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 359 days.

(21) Appl. No.: 10/805,775

(22) Filed: Mar. 22, 2004

(65) Prior Publication Data

US 2005/0228420 A1    Oct. 13, 2005

(51) Int. Cl.
A61B 17/32    (2006.01)
A61B 17/14    (2006.01)

(52) U.S. Cl. .................... 606/167; 606/181
(58) Field of Classification Search ........... 606/166, 606/167, 181–185; 7/158; 30/153, 155, 30/61, 71, 151–164, 286, 539, 541, 51–55
See application file for complete search history.

(56) References Cited

U.S. PATENT DOCUMENTS

| 469,783 | A |  | 3/1892 | Graves |
| 1,195,169 | A |  | 8/1916 | Adcock |
| 1,914,153 | A |  | 6/1933 | Ogden |
| 2,280,463 | A | * | 4/1942 | Williamson ............ 7/158 |
| 2,304,332 | A |  | 12/1942 | Bodkin |
| 2,611,178 | A |  | 9/1952 | Whipple et al. |
| 2,735,176 | A |  | 2/1956 | Costin |
| 2,885,780 | A |  | 5/1959 | Campbell |
| 2,960,769 | A |  | 11/1960 | Matwijcow |
| 3,025,598 | A |  | 3/1962 | Nissen |
| 3,412,467 | A |  | 11/1968 | Matwijcow |
| 3,657,812 | A |  | 4/1972 | Lee |
| 3,706,106 | A |  | 12/1972 | Leopoldi |
| 3,889,368 | A |  | 6/1975 | Himeno |
| 3,905,101 | A |  | 9/1975 | Shepherd |
| 3,906,626 | A |  | 9/1975 | Riuli |
| 3,943,627 | A |  | 3/1976 | Stanley, Jr. |
| 4,091,537 | A |  | 5/1978 | Stevenson, Jr. |
| 4,393,587 | A |  | 7/1983 | Kloosterman |
| 4,414,974 | A |  | 11/1983 | Dotson et al. |
| 4,491,132 | A |  | 1/1985 | Aikins |
| 4,499,898 | A |  | 2/1985 | Knepshield et al. |
| 4,516,575 | A |  | 5/1985 | Gerhard et al. |
| 4,523,379 | A |  | 6/1985 | Osterhout et al. |

(Continued)

FOREIGN PATENT DOCUMENTS

DE    37 22 899 A1    1/1989

(Continued)

*Primary Examiner*—Glenn K. Dawson
*Assistant Examiner*—Kathleen Sonnett

(57) ABSTRACT

A surgical scalpel assembly includes a handle having at least one attachment element and at least one guide element. The assembly also has a guard including at least one guide member configured to engage the at least one guide element of the handle such that the guard is movably connectable with the handle. The guard includes a first biased arm having a first boss and a second cantilevered arm having a second boss. The assembly also includes a blade having an attachment groove configured to engage the attachment element of the handle. The blade includes a first hole configured to receive the first boss when the blade is connected to the guard and a second hole configured to receive the second boss when the blade is connected to the guard.

28 Claims, 8 Drawing Sheets

U.S. PATENT DOCUMENTS

| | | |
|---|---|---|
| 4,538,356 A | 9/1985 | Knepshield et al. |
| 4,576,164 A | 3/1986 | Richeson |
| 4,630,378 A | 12/1986 | Kulp et al. |
| 4,660,287 A | 4/1987 | Decker |
| 4,662,075 A | 5/1987 | Mastel et al. |
| 4,719,915 A | 1/1988 | Porat et al. |
| 4,735,202 A | 4/1988 | Williams |
| 4,757,612 A | 7/1988 | Peyrot |
| 4,768,509 A | 9/1988 | Grosvenor et al. |
| 4,803,751 A | 2/1989 | Cousins |
| 4,805,304 A | 2/1989 | Knoop |
| 4,815,218 A | 3/1989 | Gordy |
| 4,823,457 A | 4/1989 | Prochaska |
| 4,825,545 A | 5/1989 | Chase et al. |
| 4,949,458 A | 8/1990 | Davis et al. |
| 4,985,034 A | 1/1991 | Lipton |
| 5,015,252 A | 5/1991 | Jones |
| 5,035,703 A | 7/1991 | Baskas |
| 5,071,426 A | 12/1991 | Dolgin et al. |
| 5,116,351 A * | 5/1992 | Frassetti ............. 606/167 |
| 5,139,507 A | 8/1992 | Dolgin et al. |
| 5,201,748 A | 4/1993 | Newman et al. |
| 5,207,696 A | 5/1993 | Matwijcow |
| 5,250,063 A | 10/1993 | Abidin et al. |
| 5,250,064 A | 10/1993 | Schneider |
| 5,258,001 A | 11/1993 | Corman |
| 5,275,606 A | 1/1994 | Abidin et al. |
| 5,292,329 A | 3/1994 | Werner |
| 5,299,357 A | 4/1994 | Wonderley et al. |
| 5,309,641 A | 5/1994 | Wonderley et al. |
| 5,342,379 A | 8/1994 | Volinsky |
| 5,344,424 A | 9/1994 | Roberts et al. |
| 5,411,512 A | 5/1995 | Abidin et al. |
| 5,417,704 A | 5/1995 | Wonderley |
| 5,527,329 A | 6/1996 | Gharibian |
| 5,569,281 A | 10/1996 | Abidin et al. |
| 5,676,677 A * | 10/1997 | Landis et al. ............. 606/167 |
| 5,868,771 A * | 2/1999 | Herbert et al. ............. 606/167 |
| 5,919,201 A | 7/1999 | Carter et al. |
| 5,938,675 A | 8/1999 | Gharibian |
| 5,938,676 A | 8/1999 | Cohn et al. |
| 6,053,929 A | 4/2000 | Cohn et al. |
| 6,574,868 B1 * | 6/2003 | Overholt .................. 30/155 |
| 6,626,925 B2 | 9/2003 | Newman et al. |
| 6,629,985 B1 * | 10/2003 | Kiehne .................. 606/167 |

FOREIGN PATENT DOCUMENTS

| WO | WO 01/05312 A1 | 1/2001 |
|---|---|---|

* cited by examiner

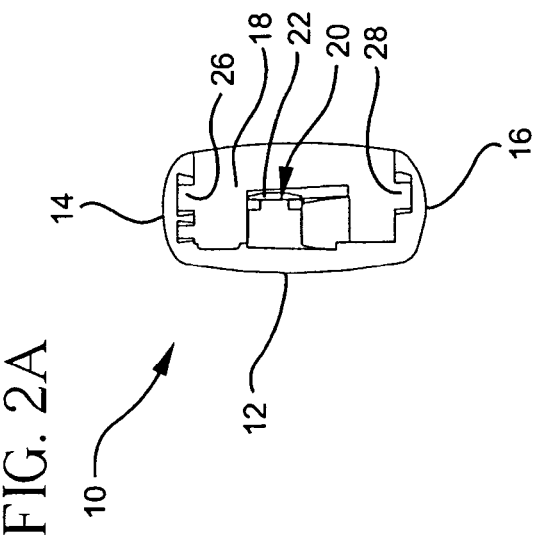
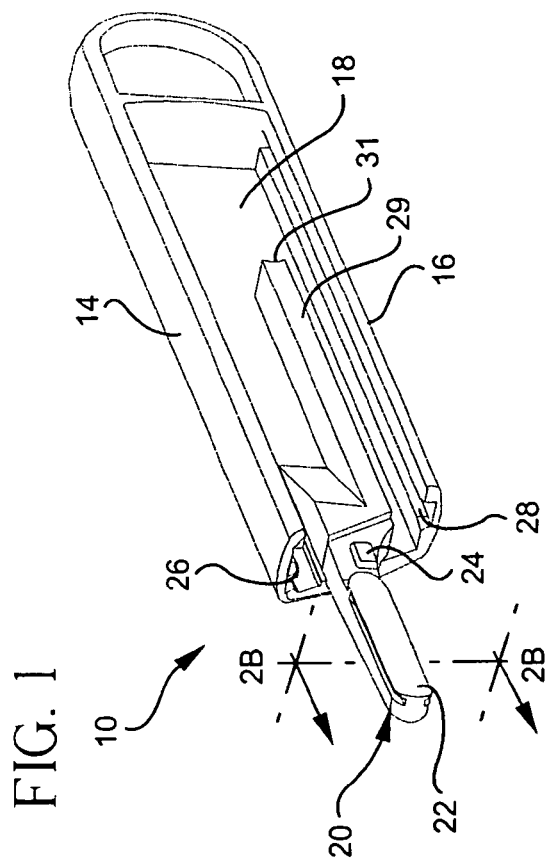

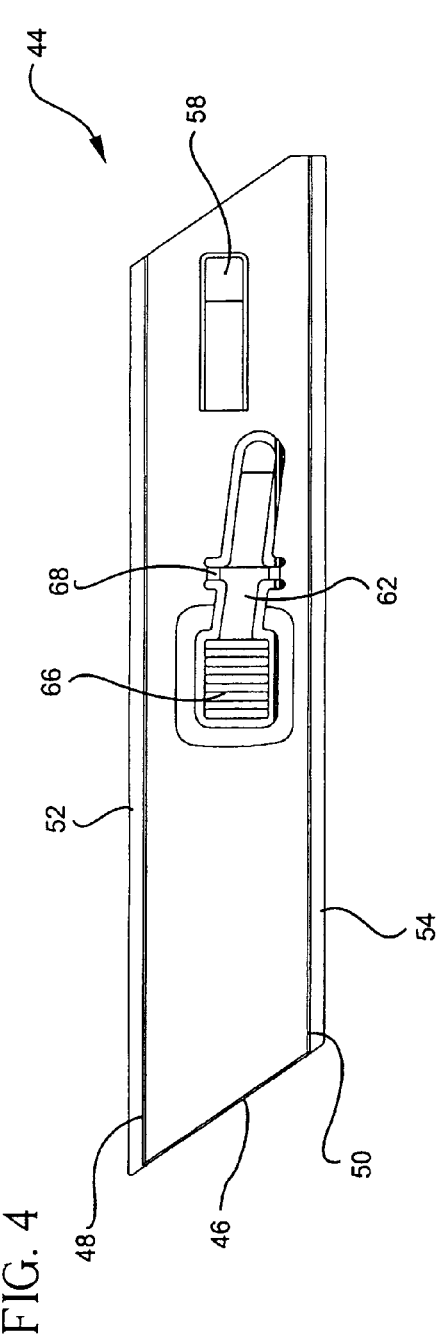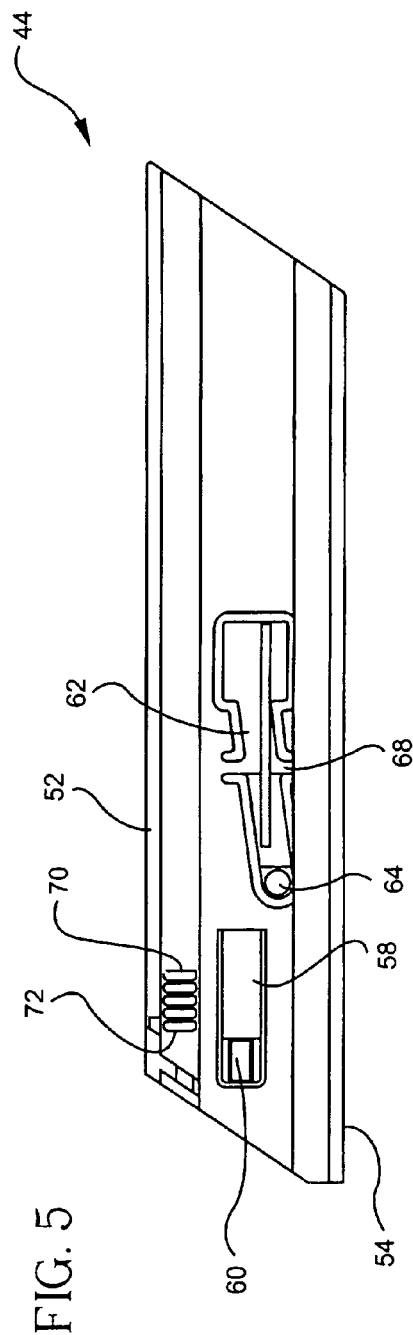
FIG. 4
FIG. 5

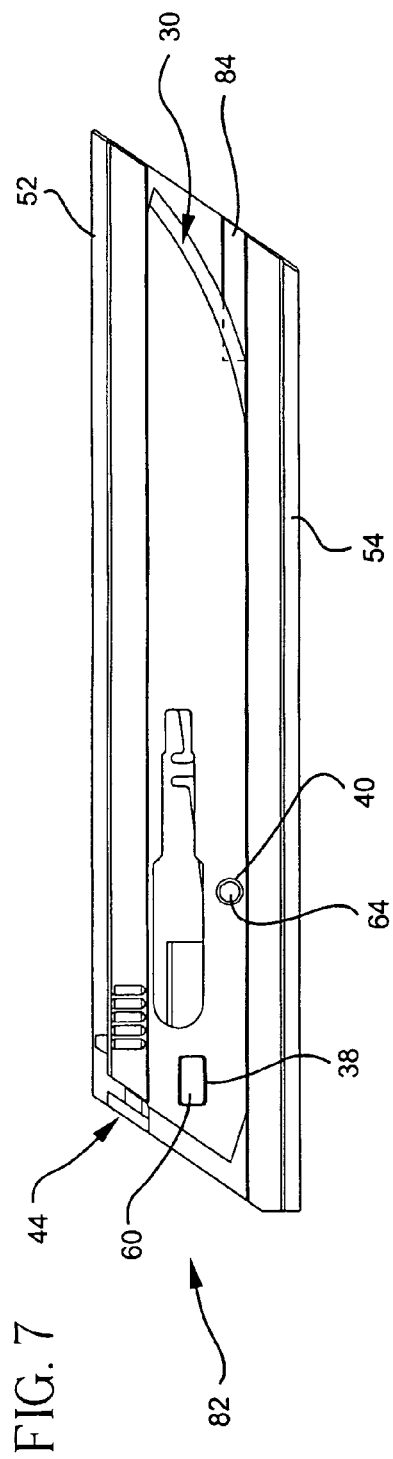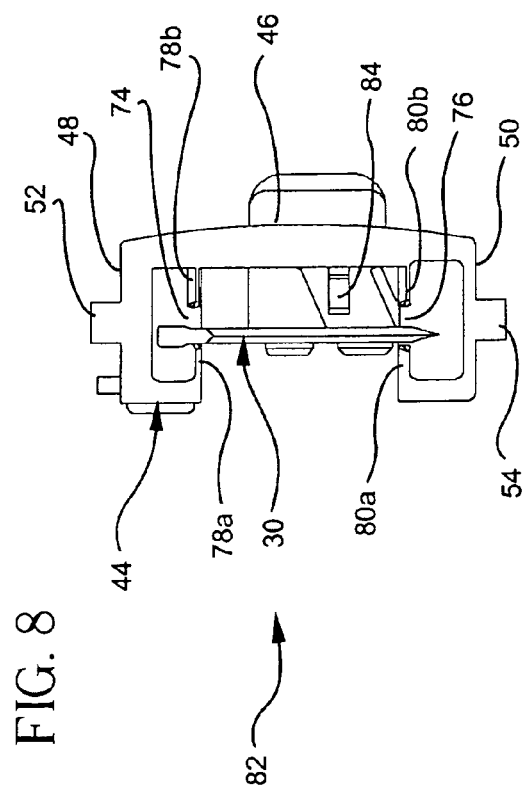

SURGICAL SCALPEL ASSEMBLY

BACKGROUND OF THE INVENTION

1. Field of the Invention

This invention relates generally to surgical scalpels and, more particularly, to surgical scalpels having shields or guards to cover the scalpel blade when not in use.

2. Technical Considerations

As will be appreciated by one skilled in the medical arts, sharp surgical instruments, such as scalpels, provide a significant potential for harm to surgeons, nurses, and other support personnel. The rapid handling of these sharp instruments can lead to accidental cuts or puncture wounds during surgery. In order to address this problem, blade shields have been developed to cover the scalpel blade when the scalpel is not in use. The shields can be retracted to expose the blade when needed.

While early blade shields did help reduce the potential for accidental cuts or puncture wounds, there were some problem areas. For example, some of the blade shields were awkward to operate, often requiring two hands to operate. Others included complex mechanical mechanisms to move the shield, which mechanisms could be prone to mechanical failure.

Improved scalpel blade protection devices were subsequently developed to address these issues. These scalpel systems provide improved handling and safety features compared to the earlier devices. For example, U.S. Pat. No. 6,053,929 discloses a surgical scalpel system having a handle and a cartridge removably mounted on the handle. The cartridge includes a blade holder and a shield. Another surgical scalpel is disclosed in PCT WO 01/05312. This scalpel has a handle that can be attached to a guard containing the scalpel blade. Examples of other known scalpels having blade shields or covers are disclosed in U.S. Pat. Nos. 5,250,064; 5,342,379; 5,527,329; 5,938,675; 5,938,676; and 5,919,201. While these systems provide some advantages over the earlier blade protection devices, improvements could still be made to these devices.

Therefore, it is an object of the invention to provide a surgical scalpel assembly that reduces the complexity of prior known scalpel devices and which also provides additional safety and manufacturing benefits over known scalpel systems.

SUMMARY OF THE INVENTION

A surgical scalpel assembly of the invention comprises a handle having at least one attachment element and at least one guide element. The assembly further includes a guard comprising at least one guide member configured to engage the at least one guide element of the handle such that the guard is movable on the handle between a first position and a second position. The guard can include a first biased arm having a first boss, and a second movable, e.g., cantilevered, arm having a second boss. The assembly additionally comprises a blade having an attachment groove configured to engage the attachment element of the handle. The blade can include a first hole configured to receive the first boss when the blade is connected to the guard and the handle is not attached to the blade, and a second hole configured to receive the second boss when the blade is connected to the guard and the guard is in the first position.

Another surgical scalpel assembly of the invention comprises a handle comprising a blade carrier having a blade attachment element. A guard of the assembly comprises a retaining arm having a non-arcuate retaining boss. A blade of the assembly comprises a slot configured to engage the attachment element of the blade carrier, and a retaining hole having a non-arcuate shape and configured to engage the retaining boss of the guard.

A further surgical scalpel assembly of the invention comprises a handle having a handle body with a blade attachment element projecting therefrom. The handle can have a side wall, a top wall, and a bottom wall defining a handle cavity. Guide grooves are defined in the top wall and bottom wall. A guard of the assembly comprises a guard body having a top wall; a bottom wall, and a side wall defining a guard cavity. A guide rail projects from the top wall and bottom wall of the guard and the guide rails are configured to engage the guide grooves in the handle body such that the guard is slidable into and out of the handle body. The guard further includes a first or retaining arm biased inwardly from the guard side wall, with a first retaining boss attached to the retaining arm. The retaining boss has a non-arcuate cross section. A second or locking arm can be biased inwardly from the guide sidewall. The locking arm can be a movable, e.g., cantilevered, arm with a locking boss attached at one end. A blade deflection device can be movably mounted on the guard. A blade of the assembly comprises an elongated attachment slot configured to engage the blade attachment element of the handle, a first hole configured to engage the first boss of the first (retaining) arm, and a second hole configured to receive the second boss of the second (locking) arm.

A still further surgical scalpel assembly of the invention comprises a blade having a pair of rear arms, each arm having an engagement member and an attachment member. A guard has a pair of engagement elements configured to engage the engagement members of the blade arms to bias the arms outwardly. A handle has a pair of attachment elements configured to engage the attachment members of the blade when the handle is inserted between the blade arms.

Another surgical scalpel assembly comprises a handle and a blade and guard assembly. The blade and guard assembly comprises a guard comprising a first biased arm having a first boss, a second movable, e.g., cantilevered, arm having a second boss, and a blade having an attachment member configured to engage the handle. The blade further includes a first hole configured to receive the first boss when the blade is connected to the guard and the handle is not attached to the blade, and a second hole configured to receive the second boss when the blade is in the guard.

An additional surgical scalpel assembly comprises a handle having a blade attachment element, a blade having an attachment member configured to engage the attachment element of the handle, and a guard configured to engage the handle. The guard includes a blade deflection device.

A further surgical scalpel assembly comprises a handle having a blade attachment element and a locking device, a blade having a locking element and an attachment element, and a guard having a locking arm configured to engage the locking element of the blade when the guard is in a first position and configured to engage the locking device of the handle when the guard is in a second position.

A blade and guard assembly of the invention comprises a guard with a first biased arm having a first boss, a second movable, e.g., cantilevered, arm having a second boss, and a blade. The blade includes an attachment member configured to engage the handle, a first hole configured to receive the first boss when the blade is connected to the guard and the handle is not attached to the blade, and a second hole configured to receive the second boss when the blade is in the guard.

BRIEF DESCRIPTION OF THE DRAWINGS

Additional advantages and details of the invention are explained in greater detail below with reference to the exemplary embodiments illustrated in the accompanying schematic drawings, in which:

FIG. 1 is a perspective view of a scalpel handle incorporating features of the invention;

FIG. 2A is a front view of the handle of FIG. 1;

FIG. 4 is a side view (closed side) of a guard incorporating features of the invention;

FIG. 5 is a side view (open side) of the guard of FIG. 4;

FIG. 7 is a side view of the guard of FIG. 5 with the blade positioned in the guard;

FIG. 8 is a front view of the blade and guard assembly of FIG. 7;

DESCRIPTION OF THE PREFERRED EMBODIMENTS

Figure 2B:
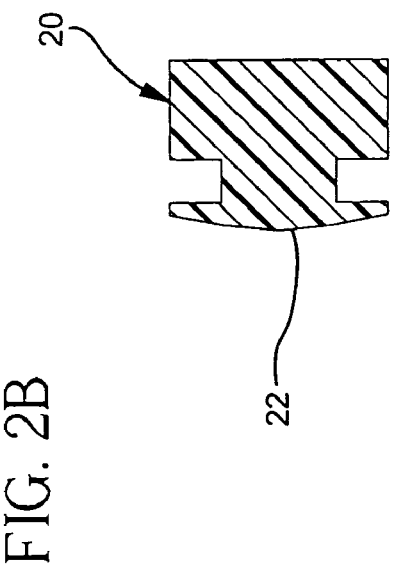
FIG. 2B is a sectional view taken along the line IIB-IIB of FIG. 1.

As used herein, spatial or directional terms, such as "front", "rear", "left", "right", and the like, relate to the invention as it is shown in the drawing figures. However, it is to be understood that the invention can assume various alternative orientations and, accordingly, such terms are not to be considered as limiting. Additionally, all references referred to in this document are to be understood as being incorporated by reference in their entirety.

The individual components of an exemplary surgical scalpel assembly incorporating features of the invention will first be described and then operation of the exemplary scalpel assembly will be discussed. However, it is to be understood that the exemplary scalpel assembly described herein is simply to illustrate the general features of the invention and that the invention is not limited to the specifically disclosed exemplary embodiments.

A scalpel handle 10 of the invention is shown in FIGS. 1, 2A, and 2B. The handle 10 can be made of any desired material, such as but not limited to plastics, metal, etc., and can be of any desired dimensions. In the illustrated embodiment, the handle 10 has a substantially "C" shaped profile in cross section (i.e., has a substantially closed side and a substantially open side). The handle 10 has a first side wall 12, a top wall 14, and a bottom wall 16 that define an interior hollow space or cavity 18 within the handle 10. The handle 10 can be made of a single piece of material, such as metal, with the side wall 12, top wall 14, and bottom wall 16 being of a unitary structure. The handle 10 can have a second side wall opposite the first side wall 12 or, as shown in the exemplary embodiment, the second side of the handle 10 (opposite the first side wall 12) can be open.

The handle 10 further includes a blade carrier 20 configured to engage a surgical blade as described in more detail below. In the exemplary embodiment, the blade carrier 20 is formed as a conventional projection or "finger" extending from the front of the handle 10. The finger includes an attachment element 22 configured to engage a portion of the blade to hold the blade onto the handle 10 in conventional manner. In the illustrated embodiment, the attachment element 22 is configured as a raised portion extending from the side of the finger. However, in the broad practice of the invention, any conventional attachment means could be used. The handle 10 further includes an unlocking element 24. In the illustrated embodiment, the unlocking element 24 is formed by a projection extending outwardly from the side of the finger to the rear of the attachment element 22.

As shown particularly in FIG. 2A, the handle 10 also includes at least one guide member to receive a blade guard as described in more detail below. The guide member(s) can be of any conventional design. However, in the illustrated exemplary embodiment, the guide members are configured as opposed grooves 26, 28 formed in the top wall 14 and bottom wall 16, respectively, of the handle 10 and extend at least partly along the length of the interior of the top wall 14 and bottom wall 16.

The handle 10 can also include a guard locking device to allow the guard to be locked in a retracted position, i.e., such that at least a portion of the blade is exposed. In the illustrated exemplary embodiment, the locking device is configured as a rib 29 extending along the handle cavity 18. The rib 29 includes an end surface 31 configured to engage a locking element, e.g., a locking boss, on the guard as described in more detail below. However, in the broad practice of the invention, any conventional device to retain the guard in a retracted position could be used.

Figure 3:
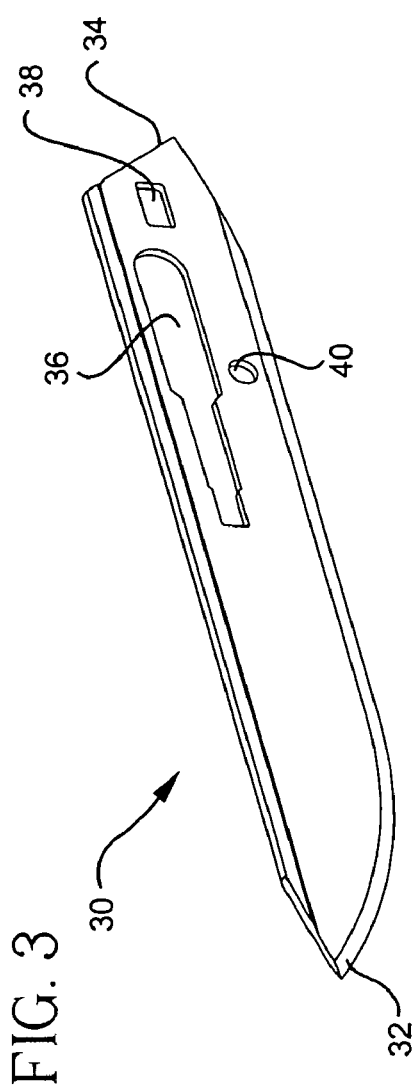
FIG. 3 is a perspective view of a blade incorporating features of the invention.

A blade 30 incorporating features of the invention is shown in FIG. 3. The blade 30 can be of any conventional length or dimensions as are well known in the surgical art. The blade 30 has a front 32 and a rear 34 and includes an attachment member 36 configured to engage the attachment element 22 of the blade carrier 20 to attach the blade 30 to the handle 10. In the illustrated embodiment, the attachment member 36 is configured as a conventional slot having a wider portion and a narrower portion configured to releasably engage the attachment element 22 on the handle 10. Such a conventional blade slot is well known in the art and will not be described in detail.

However, in one non-limiting practice of the invention, the blade 30 can further include a retaining element, such as a first or retaining hole 38 positioned near the rear 34 of the blade 30. While in the broad practice of the invention the retaining hole 38 can be of any shape, as will be described below it is particularly advantageous if the retaining hole 38 is of a non-arcuate shape. By "non-arcuate" is meant that the retaining hole 38 does not have a round or curved shape, such as a circular shape, but rather has one or more straight sides, such as a quadrilateral shape, for example a square or rectangular shape. In another non-limiting embodiment, the blade 30 may not have a separate retaining hole 38 but, rather, the attachment member 36 can be configured to receive a retaining device, as described in more detail below.

The blade 30 can further include a locking element, such as a second or locking hole 40 which can be positioned forward of the retaining hole 38. The locking hole 40 can be of any desired shape but in the illustrated embodiment the locking hole 40 has an arcuate shape, i.e., a round shape.

A guard 44 incorporating features of the invention is shown in FIGS. 4–8. In the illustrated embodiment, the guard 44 can be substantially "C" shaped in cross section and can have a side wall 46, a top wall 48, and a bottom wall 50 (FIG. 8). The guard 44 can be made of any desired material, such as metal, plastic, or a combination of metal and plastic. However, it is to be understood that the guard 44 is not limited to this configuration but could have a closed structure, i.e., a second side wall opposite the first side wall 46. The guard 44 includes at least one guide element configured to engage the at least one guide member in the handle 10 as described in more detail below. In the illustrated embodiment, the guide element(s) are configured as ribs or rails 52, 54 extending outwardly from the top wall 48 and bottom wall 50, respectively, of the guard 44. However, it is to be understood that this is simply one exemplary configuration for the guide elements and that the invention is not limited to these specific guide elements.

The guard 44 can further comprise a first or retaining arm 58 which can be formed integrally with the side wall 46. The retaining arm 58 can be of any desired shape and includes a retaining boss 60 located at or near the inner end of the retaining arm 58. In the illustrated embodiment, the retaining boss 60 is substantially rectangular in shape. The retaining boss 60 is configured to engage the retaining hole 38 in the blade 30, as described below. The portion of the retaining arm 58 with the retaining boss 60 can be biased inwardly, i.e., toward the interior of the guard 44, in any conventional manner.

The guard 44 can further include a second or locking arm 62 which can be formed integrally with the guard side wall 46. The locking arm 62 can be a movable, e.g., cantilevered, arm with one end biased inwardly and having a locking boss 64 configured to engage the locking hole 40 on the blade 30 and/or the locking device (e.g., rib 29) on the handle 10 as described below. The outer end of the locking arm 62 can include a raised contact portion or button 66 which can be pushed to pivot the locking arm 62 around a pivot point 68 to move the locking boss 64 outwardly, e.g., out of the locking hole 40, to unlock the blade, as described below.

Figure 6:
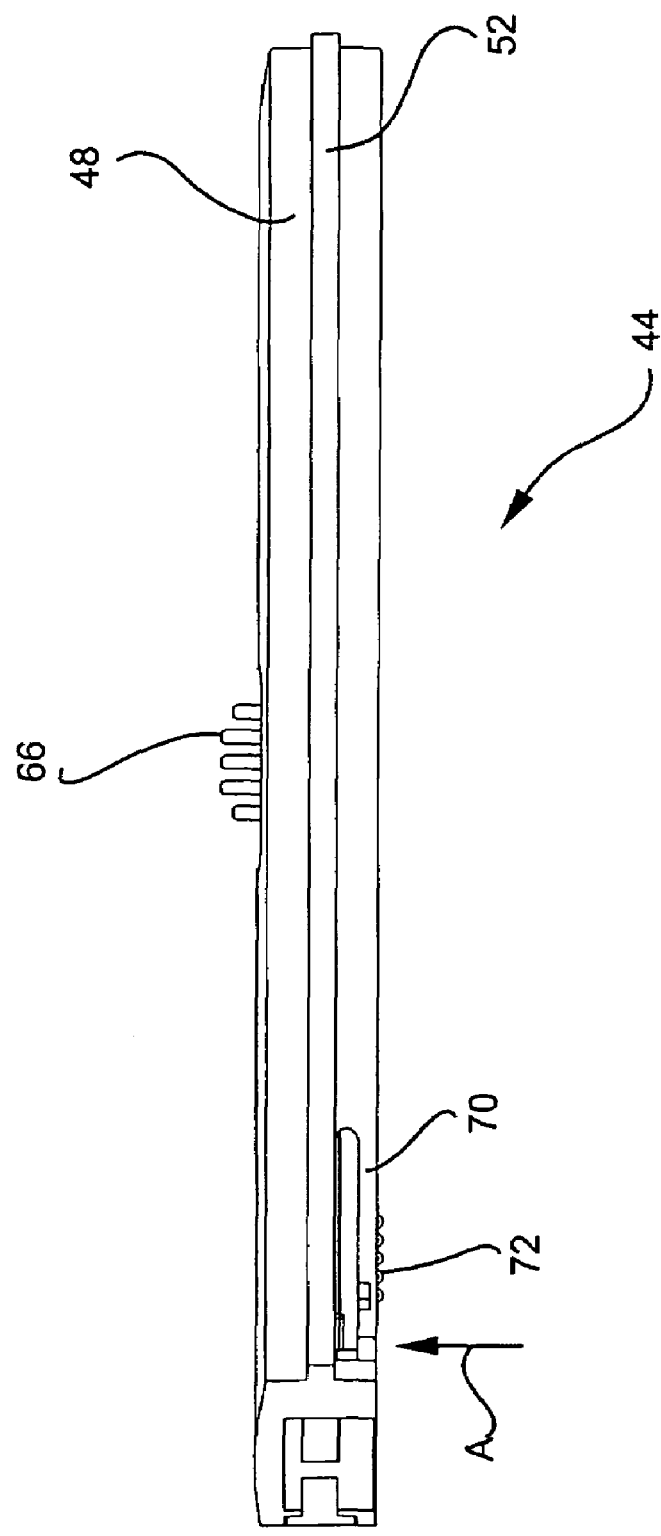
FIG. 6 is a top view of the guard of FIG. 5.

The guard 44 can further include a blade deflection device 70 (FIGS. 5 and 6). In the illustrated exemplary embodiment, the blade deflection device 70 is formed by a section of the top wall 48 which, upon the application of pressure by a user, can be bent inwardly (in the direction of arrow A in FIG. 6) as described below. The outer surface of the blade deflection device 70 can include a contact portion 72 having ribs for easier gripping and movement of the deflection device 70.

FIGS. 7 and 8 show a blade 30 positioned within the guard 44. As can be seen particularly in FIG. 8, the blade 30 can be guided in the guard 44 by upper and lower channels 74, 76. The channels 74, 76 can be defined by opposed sets of upper ribs 78a, 78b and lower ribs 80a, 80b. The blade can be positioned in the guard 44 such that the retaining boss 60 of the retaining arm 58 releasably engages the retaining hole 38 on the blade 30 and presses the blade 30 against one side of the guide ribs 78a, 80a to retain the blade 30 in the guard 44. The non-arcuate shape of the retaining hole 38 and retaining boss 60 helps prevent accidental slipping or rotation of the blade 30 around the retaining boss 60. Additionally, the locking boss 64 engages the locking hole 40 on the blade 30. This provides an additional safety feature preventing accidental withdrawal of the blade 30 from the guard 44. In the practice of the invention, the individual blade 30 and guard 44 components can be supplied separately or the guard 44 and blade 30 can be supplied as a pre-assembled unit (blade and guard assembly 82) and can be packaged in a sterile container, such as a foil container, and stored until desired.

In another non-limiting embodiment, the blade 30 need not have a separate retaining hole 38 but, rather, the retaining boss 60 can be configured to engage the attachment slot 36 of the blade 30.

The guard 44 can further include a blade retention device 84 (FIGS. 7 and 8) configured to prevent accidental disengagement of the blade 30 from the handle 10 when the guard 44 is in a retracted position, as described below. In the illustrated embodiment, the blade retention device 84 is configured as a projection or thicker portion of the guard 44 formed near the front of the guard 44.

Operation and use of the exemplary surgical scalpel assembly of the invention described above will now be described.

In order to attach the blade and guard assembly 82 to the handle 10, the attachment element 22 (projection) on the handle finger is guided into the attachment member 36 (slot) in the blade 30 and pushed forward in conventional manner. This is done by initially positioning the handle 10 at an angle with respect to the blade 30. This attachment method is well known in the surgical field and will not be described in detail. As the handle 10 is pushed forwardly with respect to the guard 44, the attachment element 22 (projection) slides into the slot 36 until the unlocking element 24 aligns with the retaining hole 38 on the blade 30 and pushes the retaining boss 60 out of the retaining hole 38 to snap the blade 30 onto the finger. In this position, the attachment element 22 of the handle 10 is engaged with the attachment member 36 of the blade 30 and the unlocking element 24 is engaged in the retaining hole 38. Additionally, the locking boss 64 engages the locking hole 40.

Figure 9:
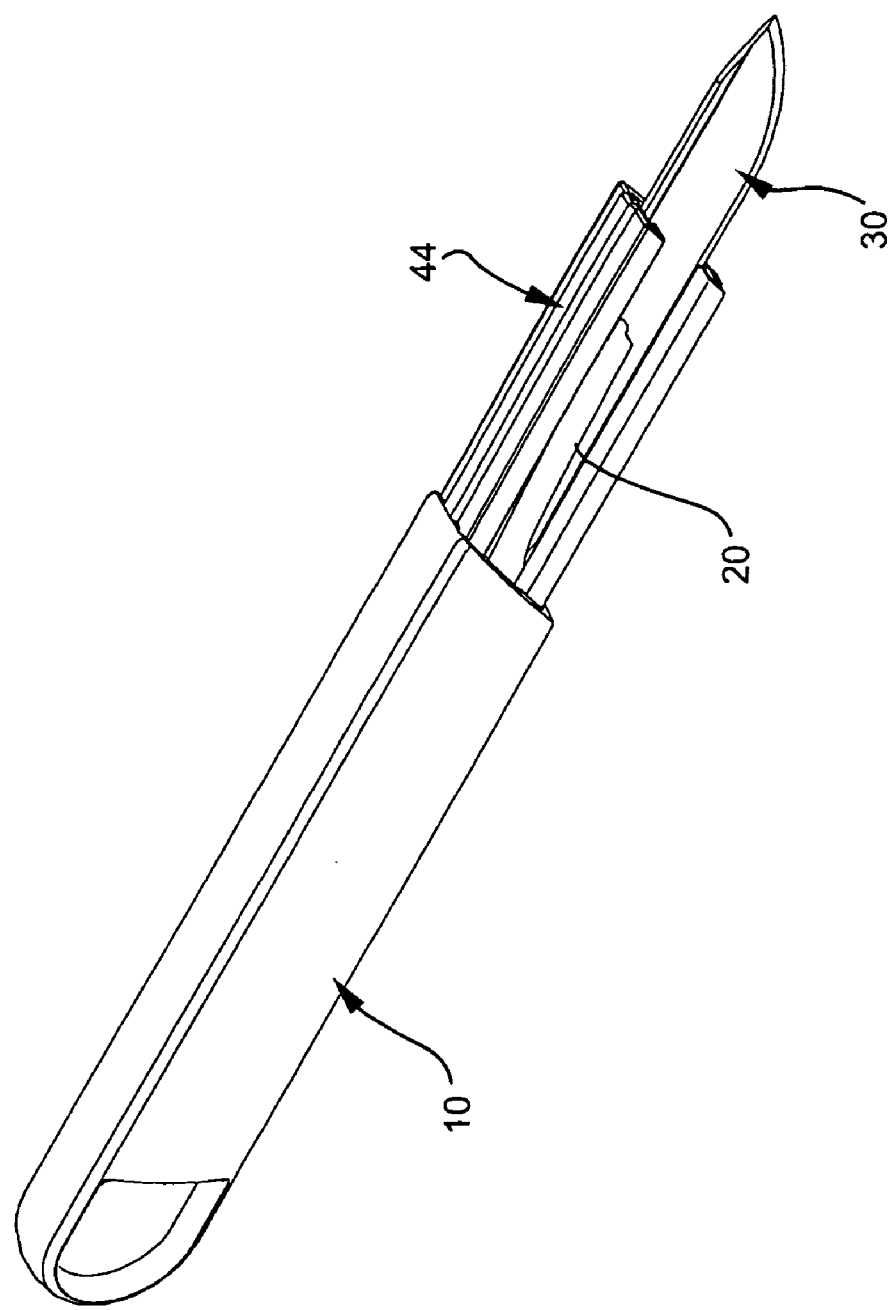
FIG. 9 is a perspective view of the handle attached to the blade and guard assembly of FIG. 7 with the guard partially retracted into the handle.
Figure 10:
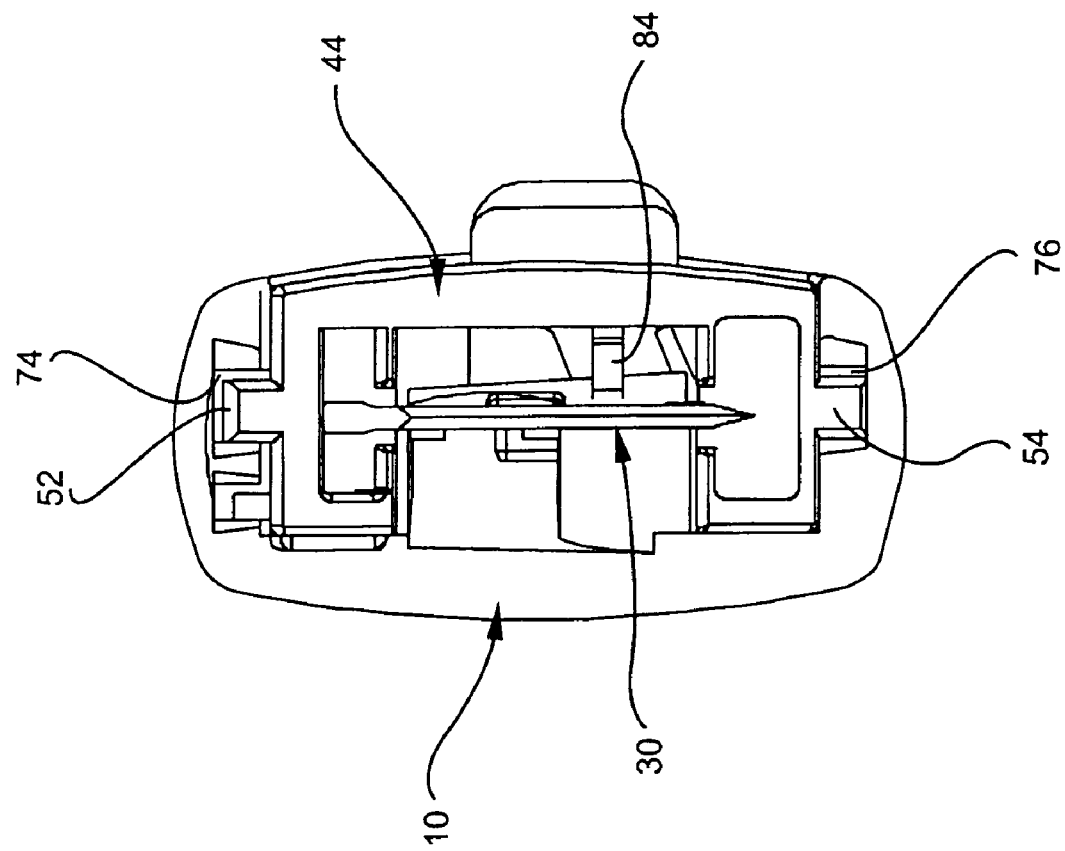
FIG. 10 is a front view of the surgical scalpel assembly of FIG. 9.

The guide elements (rails 52, 54) on the guard 44 slide into the guide channels 74, 76 on the handle 10 such that the guard 44 can slide from a first position in which the guard 44 covers the cutting edge of the blade 30 to a second position in which the guard 44 is retracted into the internal cavity 18 of the handle 10 to uncover at least a portion of the cutting edge of the blade 30, as shown in FIGS. 9 and 10. However, as will be appreciated by one skilled in the art, once the blade 30 is attached to the handle 10, the guard 44 cannot initially be retracted into the handle 10 because the locking boss 64 is engaged in the locking hole 40 of the blade 30. This prevents accidental movement of the guard 44 into the handle 10 and accidental exposure of the blade 30 until the locking boss 64 is released. In order to slide the guard 44 into the handle 10 and expose the blade 30, the operator can press on the button 66 of the locking arm 62 to pivot the locking boss 64 out of the locking hole 40 in the blade 30. This allows the guard 44 to be slid into the interior of the handle 10, exposing the blade 30. The scalpel assembly can then be used as intended. As will be appreciated from FIGS. 1 and 9, as the guard 44 is retracted into the handle 10, the locking boss 64 slides along the outer surface of the locking rib 29. When the guard 44 reaches a predetermined position, the locking boss 64 drops behind or engages the end surface 31 on the locking rib 29 due to the inward bias of the locking arm 62. This locks the guard 44 in the retracted position and prevents the guard 44 from accidentally sliding forward on the handle 10 when the scalpel is being used. In order to unlock the guard 44 from the retracted position, the button 66 on the locking arm 62 can be pushed to rotate the locking boss 64 out of engagement with the end surface 31 to allow the guard 44 to be slid forwardly on the handle 10 to again cover the blade 30. The guard 44 can be slid forwardly until the locking boss 64 re-engages the locking hole 40 to lock the guard 44 in its extended position. Between uses, the guard 44 can be slid forward, i.e., out of the handle 10, to cover the cutting edge of the blade 30.

In order to prevent accidental disengagement of the blade 30 from the handle 10 when the guard 44 is retracted into the handle 10, the blade retention device 84 on the front of the guard 44 abuts or contacts the rear 34 of the blade 30 when the guard 44 is in the retracted position. This prevents deflection of the rear 34 of the blade 30 and, hence, prevents accidental disengagement of the finger from the blade slot 36 when the guard 44 is retracted into the handle 10.

When use of the scalpel assembly is no longer required, the blade and guard assembly 82 can be disconnected as a unit from the handle 10 and discarded. To disengage the blade and guard assembly 82 from the handle 10, the guard 44 can be slid outwardly until the locking boss 64 engages the locking hole 40 of the blade 30. Then, the handle 10 can be tilted at an angle with respect to the blade 30 and the attachment element 22 disengaged from the blade slot 36 by pulling the handle 10 rearwardly, as is known in the art. When the handle 10 is angled outwardly, the unlocking element 24 is pulled out of the retaining hole 30. The bias on the retaining arm 58 causes the retaining boss 60 to re-engage with the retaining hole 38 to hold the blade 30 in the guard 44.

Alternatively, to help disengage the handle 10 from the slot 36, the blade deflection device 70 can be used. In order to facilitate disengagement, the deflection device 70 can be pressed inwardly (in the direction of arrow A) to push against and deflect the rear 34 of the blade 30 toward the guard side wall 46 and, thus, bend or angle the rear 34 of the blade 30 toward the side wall 46. By bending the rear 34 portion of the blade 30, this angles the rear 34 of the blade 30 with respect to the longitudinal axis of the guard 44 and facilitates removal of the handle 10 with the blade slot 36. The handle 10 can then be cleaned, such as by autoclaving, and can be reused. As will be appreciated, the deflection device 70 could also be used to aid in attaching the handle 10 to the blade 30 by bending the rear 34 of the blade 30 to provide for easier insertion of the attachment element 22 of the handle 10 into the slot 36 of the blade 30.

Figure 11:
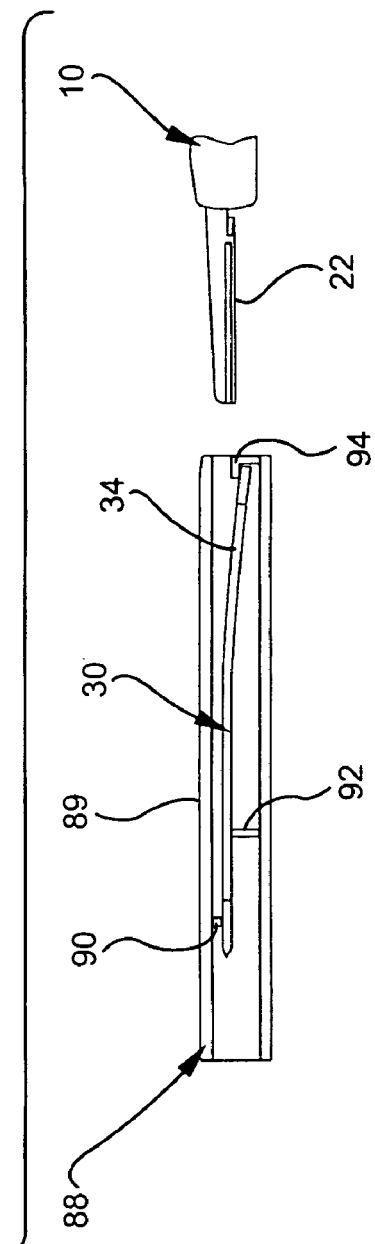
FIG. 11 is a plan view of an alternative guard incorporating features of the invention.

An alternative blade and guard assembly 88 of the invention is shown in FIG. 11. In this embodiment, the guard 89 includes opposed positioning ribs 90, 92 to align the forward portion of the blade 30. However, the guard 89 also includes a blade holding device, such as a hook or projection 94, that biases or bends the rear of the blade 30 when the blade 30 is in the guard 89. As described above, it is easier to attach a handle 10 to the blade 30 when the rear 34 of the blade 30 is deflected and, thus, presents easier access of the handle attachment element 22 with the slot 36 on the blade 30. As will be appreciated from the blade and guard assembly 88 of FIG. 11, as the handle 10 is pushed forwardly into the slot 36, the handle 10 pushes the blade 30 forward and disengages the rear 34 of the blade 30 from the projection 94 to snap the rear 34 of the blade 30 onto the finger of the handle 10.

Figure 12:
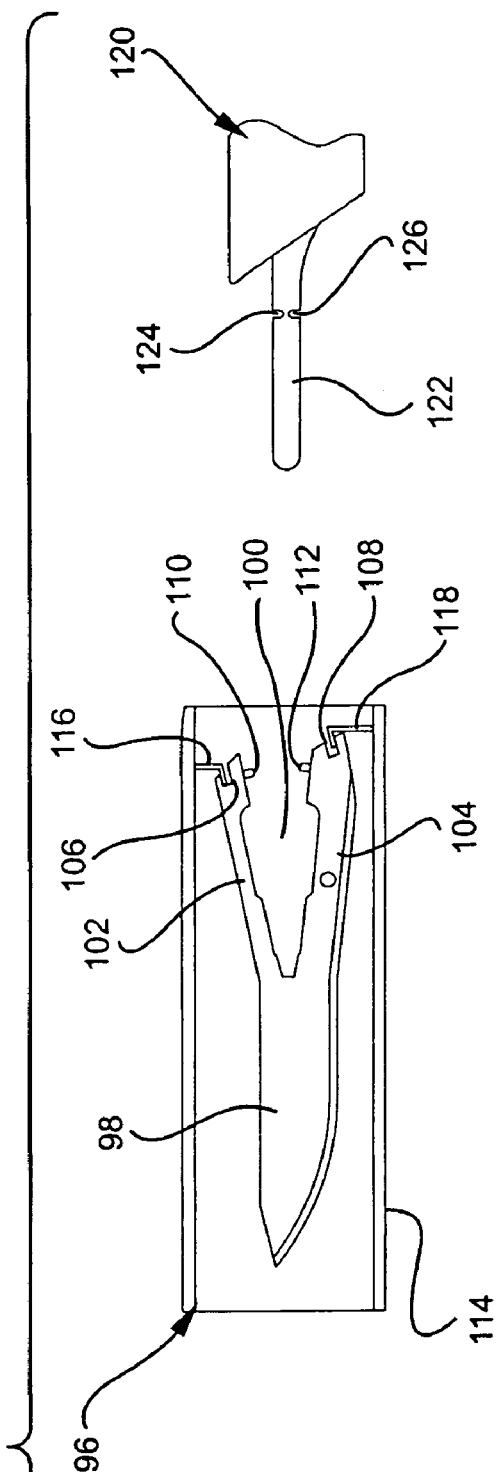
FIG. 12 is a side view of another blade and guard assembly incorporating features of the invention.

A still further blade and guard assembly 96 is shown in FIG. 12. In this embodiment, the blade 98 includes a rear engagement slot 100 defined between two rear arms 102, 104. Each arm 102, 104 includes an engagement member, such as a slot 106, 108, and an attachment member, such as a tooth or projection 110, 112. The guard 114 includes engagement elements, such as hooks 116, 118, to bias the arms 102, 104 outwardly when the blade 98 is positioned in the guard 114. The handle 120 includes a finger 122 having attachment elements, such as slots or depressions 124, 126. As the handle 120 is pushed into the guard 114, the finger 122 enters the slot 100 and pushes the blade 98 forward to disengage the hooks 116, 118 from the slots 106, 108 to cause the arms 102, 104 to snap toward each other and engage the projections 110, 112 on the blade 98 with the depressions 124, 126 on the handle 120 to lock the blade 98 onto the handle 120.

It will be readily appreciated by those skilled in the art that modifications may be made to the invention without departing from the concepts disclosed in the foregoing description. Accordingly, the particular embodiments described in detail herein are illustrative only and are not limiting to the scope of the invention, which is to be given the full breadth of the appended claims and any and all equivalents thereof.

What is claimed:

1. A surgical scalpel assembly, comprising:
   (a) a handle having at least one attachment element and at least one guide element;
   (b) a guard, comprising:
   at least one guide member configured to engage the at least one guide element of the handle such that the guard is movable on the handle between a first position and a second position;
   a first biased arm having a first boss; and
   a second movable arm having a second boss; and
   (c) a blade, comprising:
   an attachment member configured to engage the attachment element of the handle;
   a first hole configured to receive the first boss when the blade is connected to the guard and the handle is not attached to the blade; and
   a second hole configured to receive the second boss when the blade is connected to the guard and the guard is in the first position.

2. The scalpel assembly of claim 1, wherein the attachment element of the handle comprises an elongated projection extending from the handle and the attachment member of the blade comprises an elongated slot configured to receive the elongated projection.

3. The scalpel assembly of claim 1, wherein the handle is substantially "C" shaped in cross section.

4. The scalpel assembly of claim 1, wherein the at least one guide element of the handle comprises opposed grooves.

5. The scalpel assembly of claim 1, wherein the handle further comprises an unlocking element.

6. The scalpel assembly of claim 1, wherein the handle comprises a blade carrier extending from the handle, wherein the blade carrier comprises the attachment element and an unlocking element.

7. The scalpel assembly of claim 1, wherein the handle includes a locking device configured to lock the guard in the second position.

8. The scalpel assembly of claim 1, wherein the guard includes a blade deflection device configured to bend a rear portion of the blade when the blade is positioned in the guard.

9. The scalpel assembly of claim 1, wherein the guard includes a blade retention device configured to abut a rear of the blade when the guard is retracted into the handle.

10. The scalpel assembly of claim 1, wherein the at least one guide member of the guard comprises raised rails.

11. The scalpel assembly of claim 1, wherein the handle has an open front and the guard is configured to slide from the first position in which the guard covers at least a portion of the blade to the second position in which the guard is at least partly retracted into the handle to expose at least a portion of the blade.

12. The scalpel assembly of claim 1, wherein the first boss is non-arcuate in cross section.

13. The scalpel assembly of claim 1, wherein the first boss is quadrilateral in cross section.

14. The scalpel assembly of claim 1, wherein the second boss is circular in cross section.

15. The scalpel assembly of claim 1, wherein the first hole of the blade is non-arcuate in shape.

16. The scalpel assembly of claim 1, wherein the guard includes a blade holding device configured to retain a rear portion of the blade in a deflected position in the guard until the handle is attached.

17. A surgical scalpel assembly, comprising:
(a) a handle comprising a blade carrier having a blade attachment element;
(b) a guard, comprising:
a retaining arm having a non-arcuate retaining boss; and
a locking arm having a locking boss; and
(c) a blade, comprising:
a slot configured to engage the attachment element of the blade carrier;
a retaining hole having a non-arcuate shape and configured to engage the retaining boss of the guard; and
a locking hole configured to engage the locking boss.

18. The scalpel assembly of claim 17, wherein the handle comprises opposed guide channels and the guard includes rails configured to engage the guard channels such that the guard is slidable into and out of the handle.

19. The scalpel assembly of claim 17, wherein the guard includes a locking arm having a locking boss and the handle includes a locking device configured to engage the locking boss to lock the guard in a retracted position.

20. A surgical scalpel assembly, comprising:
(a) a handle, comprising:
a handle body having an attachment element projecting therefrom;
a side wall, a top wall, and a bottom wall defining a handle cavity; and
guide grooves defined in the top wall and bottom wall;
(b) a guard, comprising:
a guard body having a top wall, a bottom wall, and a side wall;
a guide rail projecting from the top and bottom walls of the guard and configured to engage the guide grooves in the handle body such that the guard is slidable into and out of the handle body;
a retaining arm biased inwardly from the guard side wall;
a retaining boss attached to the retaining arm, the retaining boss having a non-arcuate cross section;
a locking arm biased inwardly from the guide side wall, the locking arm comprising a movable arm with a locking boss attached at one end; and
a blade deflection device movably mounted on the guard; and (c) a blade, comprising:
an elongated attachment slot configured to engage the attachment element of the handle;
a retaining hole configured to engage the retaining boss of the retaining arm; and
a locking hole configured to engage the locking boss of the locking arm.

21. A surgical scalpel assembly, comprising:
(a) a handle; and
(b) a blade and guard assembly, comprising:
a guard, including:
a first biased arm having a first boss; and
a second movable arm having a second boss; and
a blade, including:
an attachment member configured to engage the handle;
a first hole configured to receive the first boss when the blade is connected to the guard and the handle is not attached to the blade; and
a second hole configured to receive the second boss when the blade is in the guard.

22. A surgical scalpel assembly, comprising:
(a) a blade having a pair of rear arms each having an engagement member and an attachment member;
(b) a guard having a pair of engagement elements configured to engage the engagement members of the blade arms to hold arms in an outward configuration ; and
(c) a handle having a pair of attachment elements configured to engage the attachment members of the blade when the handle is inserted between the blade arms.

23. A blade and guard assembly, comprising:
(a) a guard, including:
a first biased arm having a first boss; and
a second movable arm having a second boss; and
(b) a blade, including:
an attachment member configured to engage a handle;
a first hole configured to receive the first boss when the blade is connected to the guard and the handle is not attached to the blade; and
a second hole configured to receive the second boss when the blade is in the guard.

24. The blade and guard assembly of claim 23, wherein the guard includes a blade deflection device configured to bend a rear portion of the blade when the blade is positioned in the guard.

25. The blade and guard assembly of claim 23, wherein the guard includes at least one guide rail.

26. The blade and guard assembly of claim 23, wherein the first boss is non-arcuate in cross section.

27. The blade and guard assembly of claim 23, wherein the first boss is quadrilateral in cross section.

28. The blade and guard assembly of claim 23, wherein the second boss is circular in cross section.

* * * * *